(12) United States Patent
Morris et al.

(10) Patent No.: US 6,458,144 B1
(45) Date of Patent: Oct. 1, 2002

(54) METHODS FOR MANUFACTURING SKELETAL IMPLANTS

(75) Inventors: John W. Morris, Beachwood, NJ (US); Lawrence A. Shimp, Morganville, NJ (US); Mark P. Daughterty, Allenwood, NJ (US)

(73) Assignee: Osteotech, Inc., Eatontown, NJ (US)

(*) Notice: Subject to any disclaimer, the term of this patent is extended or adjusted under 35 U.S.C. 154(b) by 122 days.

(21) Appl. No.: 09/753,117

(22) Filed: Jan. 2, 2001

Related U.S. Application Data (60) Provisional application No. 60/173,646, filed on Dec. 30, 1999.

(51) Int. Cl.[7] ............................................. A61B 17/14
(52) U.S. Cl. .................................................... 606/179
(58) Field of Search .......................... 606/179, 61, 70, 606/180; 623/17, 16, 18, 16.11; 198/341.04; 209/660, 675

(56) References Cited

U.S. PATENT DOCUMENTS

| | | | |
|---|---|---|---|
| 4,341,206 A | | 7/1982 | Perrett et al. |
| 4,649,919 A | | 3/1987 | Thimsen et al. |
| 5,248,046 A | * | 9/1993 | Rollason ..................... 119/213 |
| 5,403,320 A | | 4/1995 | Luman et al. |
| 5,405,348 A | | 4/1995 | Anspach, Jr. et al. |
| 5,531,792 A | | 7/1996 | Huene |
| 5,722,977 A | | 3/1998 | Wilhelmy |
| 5,895,426 A | | 4/1999 | Scarborough et al. |
| 5,928,238 A | * | 7/1999 | Scarborough et al. ...... 408/201 |
| 6,033,438 A | | 3/2000 | Bianchi et al. |
| 6,096,081 A | * | 8/2000 | Grivas et al. ................. 606/79 |
| 6,132,472 A | | 10/2000 | Bonutti |
| 6,155,756 A | | 12/2000 | Mericle et al. |
| 6,200,347 B1 | | 3/2001 | Anderson et al. |
| 6,398,811 B1 | * | 6/2002 | McKay ..................... 623/16.11 |

OTHER PUBLICATIONS

UFTB Cortical Dowel Procurement article [Publication Date Unknown].
Univ. of Florida Tissue Bank MD–I and MD–II article [Publication Date Unknown].

* cited by examiner

*Primary Examiner*—Ismael Izaguirre
(74) *Attorney, Agent, or Firm*—Dilworth & Barrese, LLP (57) ABSTRACT

Instrumentation for manufacturing a bone dowel from human or animal cadaveric bone and instrumentation for evaluating the suitability of the bone and/or dowel for implant use after each step of the manufacturing process is provided. Such instrumentation for manufacturing a bone dowel includes a blanking or coring apparatus, a milling apparatus, a threading apparatus and a tapping apparatus. A gauge is provided to inspect and determine the suitability of the bone dowel at each step of the manufacturing process. By inspecting the dowel being manufactured after each step of the manufacturing process, time and effort which is needlessly wasted during completion of the manufacturing of dowels which are unsuitable for implant use (due to unsuitable bone and/or inaccurate machining of bone) can be avoided. Instrumentation for more accurately positioning bone and the partially manufactured dowel into the instrumentation for machining the dowel is also provided. Such instrumentation includes a gauge for positioning a piece of bone in relation to the apparatus, and mounting blocks for securing the partially manufactured dowel in relation to the milling apparatus.

3 Claims, 8 Drawing Sheets

METHODS FOR MANUFACTURING SKELETAL IMPLANTS

This application claims priority from United States provisional application Serial No. 60/173,646, filed Dec. 30, 1999, which is incorporated herein by reference.

BACKGROUND

1. Technical Field

The present disclosure relates generally to methods and instrumentation for manufacturing an implant, and more particularly to methods and instrumentation for manufacturing and inspecting an intervertebral implant formed from cadaveric human or animal bone.

2. Background to Related Art

Intervertebral implants which are formed from cadaveric human or animal bone ("bone") are well known in the art. Intervertebral implants formed of bone having a threaded dowel configuration, i.e., cylindrical, are also well known. The manufacturing or machining of a threaded intervertebral bone dowel is an involved process which includes at least a drilling or coring step, a milling step, a tapping step and a threading step. Due to the anatomical limitations of bone, each of the manufacturing steps must be precisely performed to produce a dowel having the requisite dimensions suitable for implant use. Typically, the entire manufacturing process is performed before the dowel is evaluated or inspected for suitability for implant use. Thus, where donor bone is not suitable for dowel manufacture or the donor bone has been improperly machined, much time and effort is needlessly wasted in performing additional manufacturing steps on a dowel which will never be useable as an implant.

Accordingly, a continuing need exists for methods and instrumentation for precisely manufacturing a bone dowel from a bone and for quickly identifying unsuitable bone early in the machining process to avoid undue waste of time and effort.

SUMMARY

In accordance with the present disclosure, instrumentation for manufacturing a bone dowel from human or animal cadaveric bone and instrumentation for evaluating the suitability of the bone and/or dowel for implant use after each step of the manufacturing process is provided. Such instrumentation for manufacturing a bone dowel includes a blanking or coring apparatus, a milling apparatus, a threading apparatus and a tapping apparatus. A series of gauges are provided to inspect and determine the suitability of the bone dowel at each step of the manufacturing process. By inspecting the dowel being manufactured after each step of the manufacturing process, time and effort which is needlessly wasted during completion of the manufacturing of dowels which are unsuitable for implant use (due to unsuitable bone and/or inaccurate machining of bone) can be avoided.

Instrumentation for more accurately positioning bone and the partially manufactured dowel into the instrumentation for machining the dowel is also provided. Such instrumentation includes a gauge for positioning a piece of bone in relation to the coring apparatus, and mounting blocks for securing the partially manufactured dowel in relation to the milling, threading and tapping apparatus.

BRIEF DESCRIPTION OF THE DRAWINGS

Preferred embodiments of the presently disclosed instrumentation for manufacturing and evaluating intervertebral implants are described herein with reference to the drawings, wherein.

DETAILED DESCRIPTION OF THE EXEMPLARY EMBODIMENTS

The embodiment of the methods and apparatus disclosed herein are discussed in terms of skeletal implantation and related instrumentation. It is contemplated that the present methods and apparatus for manufacturing implants find application in spinal implantation procedures whereby a fusion implant is placed into a receiving bed formed in an intervertebral space.

In one particular embodiment in accordance with the principles of the present disclosure, a procedure is described for machining and inspecting fusion implants including threaded cortical dowels. It is contemplated that the procedure may include processes such as coring a dowel, milling a dowel, tapping a dowel and threading a dowel. These processes are described in greater detail below.

Figure 1:
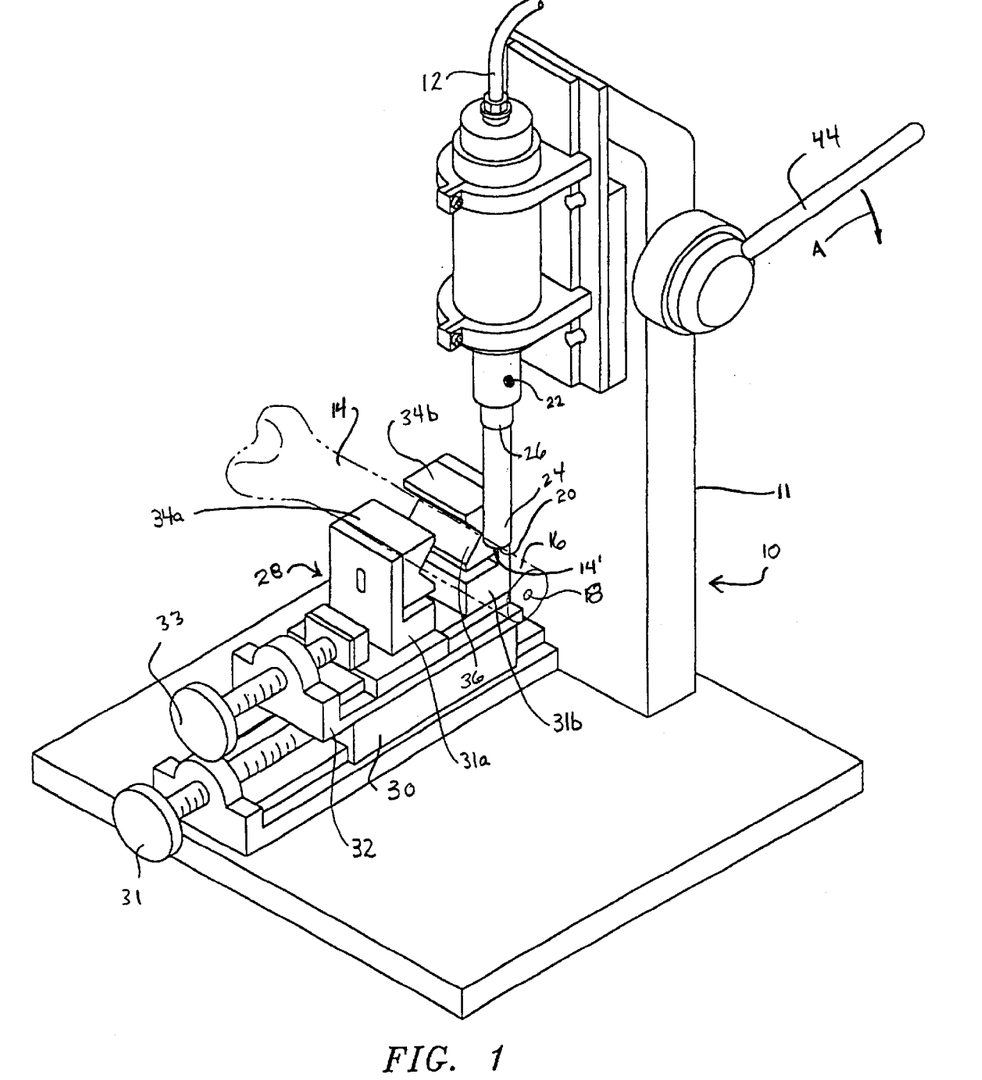
FIG. 1 is a perspective of one preferred embodiment of the presently disclosed blanking or coring apparatus.

Referring now in detail to the drawings wherein like reference numerals identify similar or like components throughout the several views, FIG. 1 illustrates aspects of a process for coring a bone dowel using a dowel coring apparatus 10.

Coring of a Dowel

A pneumatic dowel blanking or coring apparatus 10 is prepared and set up for operation prior to the coring process by connecting an air supply line 12 of dowel coring apparatus 10 to an air supply. The dowel coring apparatus 10 includes a drill press 11. Typically, an air pressure of 100 psi and above is utilized to drive a dowel cutter 24, although coring apparatus using lesser pressures may also be used. Dowel coring apparatus 10 is also attached to a water supply (not shown) for irrigation.

A bone shaft 14 is selected for producing the threaded cortical dowels. Bone shaft 14 is preferably a long bone shaft, i.e., the shaft of a femur, ulna, radius, tibia or fibula, although other bone may also be used. A cortical shaft portion 16 of bone shaft 14 includes a medullary canal 18 which is examined to determine the appropriate size dowel cutter to be used. The dowel cutter includes a hollow cylindrical bit which must be greater in diameter than the medullary canal of bone shaft 14. It is contemplated that dowel cutter sizes such as, for example, 6 mm, 8 mm, 10 mm, 12 mm, 14 mm, 16 mm, 18 mm, etc., maybe used.

After the appropriate size dowel cutter 24 is selected, it is secured to dowel coring apparatus 10. Dowel cutter 24 is secured to shaft 26 of dowel coring apparatus 10 in a known manner and includes an annular serrated edge 14. Dowel cutter 24 is configured to penetrate bone shaft 14 to blank a dowel.

Bone shaft 14 is placed into a vise assembly 28 of dowel coring apparatus 10 so that a targeted portion of shaft 14 may be blanked to produce the dowel. A first adjustment vise 30 positions bone shaft 14 along at least one axis so that canal 18 is centered with dowel cutter 24. First adjustment vise 30 is manipulated by knob 31 to adjust positioning of bone shaft 14 relative to dowel cutter 24.

Figure 9:
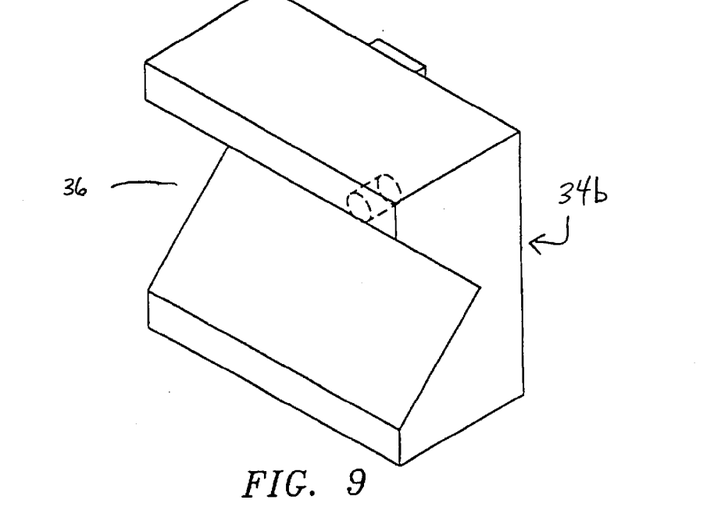
FIG. 9 is a perspective view of the support blocks of the second adjustment vise of the coring apparatus shown in FIG. 1.
Figure 10:
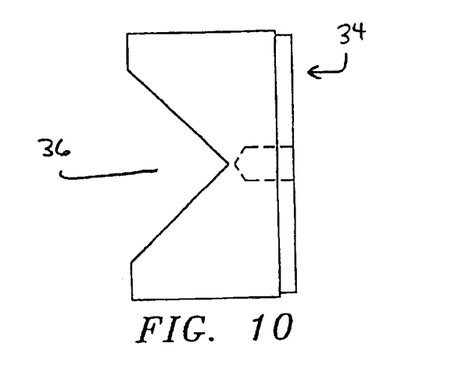
FIG. 10 is a side view of the support block shown in FIG. 9.
Figure 11:
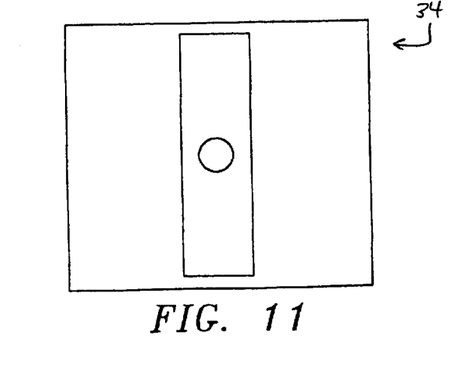
FIG. 11 is a backside view of the support block shown in FIG. 9.

A second adjustment vise 32 secures and stabilizes bone shaft 14 in position for coring. Second adjustment vise 32 includes support blocks 31a and 31b and inserts 34a and 34b. One insert is supported on each support block. Each support block is rotatably secured to vise 32 and each insert is vertically adjustable in relation to a respective support block to facilitate securement of the irregular shape of bone shaft portion 16 within vise 32. Second adjustment vise 32 is manipulated by rotating knob 33 to advance insert 34a towards insert 34b to clamp shaft portion 16 therebetween. It is contemplated that the components of the first and second adjustment vises may be movable by motorized means. Referring to FIGS. 9–11, inserts 34a and 34b have angled cavities 36 configured to receive bone shaft 14. It is contemplated that angled cavities 36 may have alternate angular configurations or may comprise other geometric configurations such as, for example, elliptical, parabolic, etc.

Figure 1A:
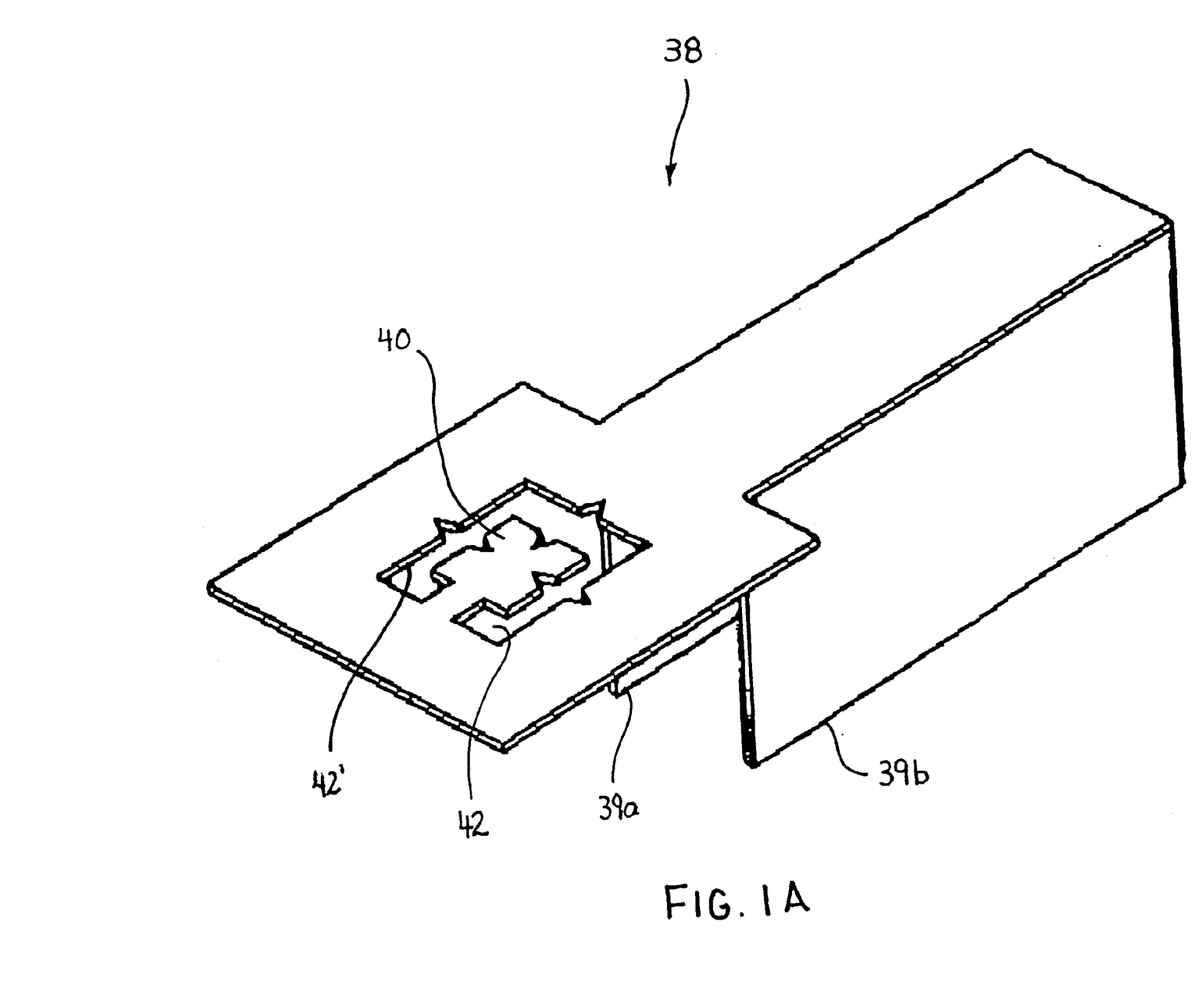
FIG. 1A is a perspective view of the presently disclosed Shimp gauge.

As illustrated in FIG. 1A, a shimp gauge 38 can be employed for properly aligning dowel cutter 24 with bone shaft 14. Shimp gauge 38 includes flexible walls 39a and 39b which are positioned on opposite sides of and snap onto dowel cutter 24. Gauge 38 includes a cross hair 40 for aligning dowel cutter 24 with the center of the medullary canal 18 of bone shaft 14. More specifically, with gauge 38 positioned about dowel cutter 24, knob 31 can be turned to adjust the position of bone shaft 14 with respect to dowel cutter 24. Bone shaft 14 should be positioned such that cross hair 40 is aligned with and positioned in front of the medullary canal at bone shaft 14. A window cavity 42 is formed about cross hair 40 and allows for a visual determination of the adequacy of thickness of cortical shaft portion 16, i.e., the cortical thickness of bone shaft 14 should cover the space between cross hair 40 and the edge 42' of window 42. To assist in visualization of canal 18 during subsequent cuts, it is suggested to remove bone shaft 14 from vise assembly 28 and saw off the previously cut end of cortical shaft portion 16.

Referring back to FIG. 1, during operation, the air and water supplies connected to dowel coring apparatus 10 are activated. As a safety feature, the air and water supplies are activated only after dowel cutter 24 is installed. A handle 44 of dowel coring apparatus 10 is manipulated, such as, for example, by gradually being pulled down in the direction indicated by arrow "A", until dowel cutter 24, which is rotating, passes through bone shaft 14. Handle 44 is thereafter released. It is contemplated that manipulation of handle 44 should be performed slowly because cutting too fast may result in off-center drilling, resulting in possible damage to the bone dowel. It is further contemplated that the components of the dowel coring apparatus may be movable by motorized means.

Figure 2:
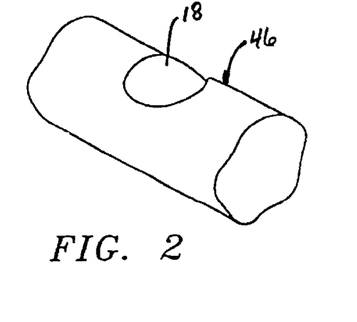
FIG. 2 is a perspective view of a bone dowel formed by the coring apparatus shown in FIG. 1.

Referring to FIG. 2, a bone dowel 46 is produced and is disposed within dowel cutter 24. Bone dowel 46, which comprises a cylindrical bone blank having a throughbore defined by medullary canal 18, may be removed from dowel cutter 24 by hand or by the use of compressed air.

Figure 12A:
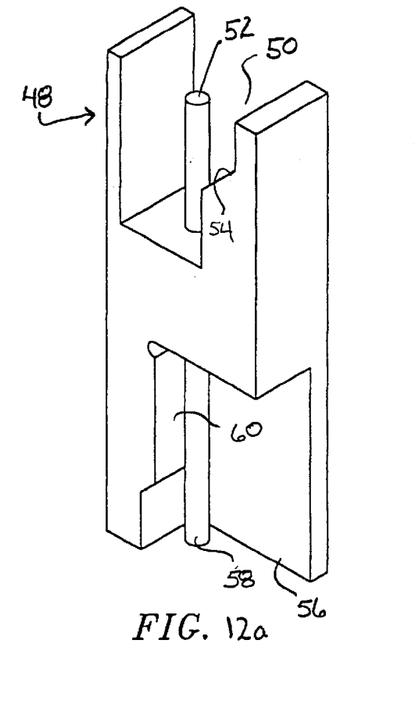
FIGS. 12a–12c are perspective, front and side views of one embodiment of the presently disclosed wall thickness GO/NO GO gauge.
Figure 12B:
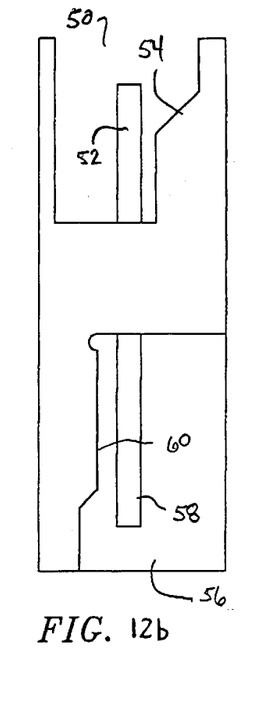
Figure 12C:
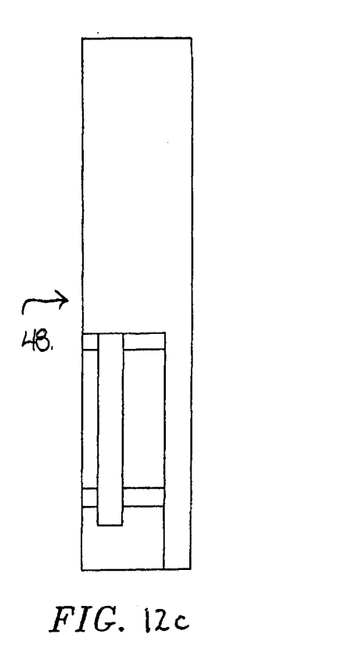

Referring to FIGS. 12A–12C, an in process check of the sidewall thickness of bone dowel 46 is performed to determine the adequacy thereof. Bone dowel 46 is rinsed in water to remove loose bone particles from its exterior and medullary canal 18. The cortical sidewall thickness of bone dowel 46 is checked using a gauge, such as the universal Wall Thickness Go/No Go gauge 48. Using a gauge end 50, which is suitably marked, e.g., "wall", medullary canal 18 of bone dowel 46 is positioned about post 52 such that the thinnest portion of the bone wall defined between medullary canal 18 and the outer circumference of bone dowel 46 is permitted to freely fall between gauge post 52 and sidewall 54 of gauge 48. Bone dowel 46 should not be forced or pushed between gauge post 52 and sidewall 54, as a false measurement for adequacy of the bone dowel may be taken. If the dowel falls to the bottom of post 52, the bone wall is too thin, and the bone dowel is rejected. This adequacy procedure is repeated for the opposite side of canal 18. If the bone dowel wall is unacceptable, i.e., rejected, bone shaft 14 should be rechecked for centering and/or a different size, i.e., larger, dowel cutter should be used. It is contemplated that reassessment of the suitability of the donor for bone dowel production may be reconsidered. If bone dowel 46 is acceptable, proceed in the manufacturing method.

Referring again to FIGS. 12A–12C, an in process check of cortical face wall thickness may be checked using the universal Wall Thickness Go/No Go gauge 48. Using gauge end 56, which is suitably marked, e.g., "Face", medullary canal 18 of bone dowel 46 is positioned onto post 58 with one end of dowel 46 positioned against face wall 60 of gauge 48 at its thinnest point. Bone dowel 46 is permitted to freely fall between gauge post 58 and face wall 60. For the reasons discussed above, bone dowel 46 should not be forced or pushed between gauge post 58 and face wall 60. If bone dowel 46 falls to the bottom of post 58, it is rejected, i.e., the wall thickness is insufficient for dowel use. If the face wall thickness of bone dowel 46 is unacceptable, bone dowel 46 is rejected and placement of bone shaft 14 in dowel coring apparatus 10 should be checked. If the bone dowel is rejected, the suitability of the donor bone for bone dowel production may be reconsidered. If bone dowel 46 is acceptable, proceed in the manufacturing method.

Figure 14:
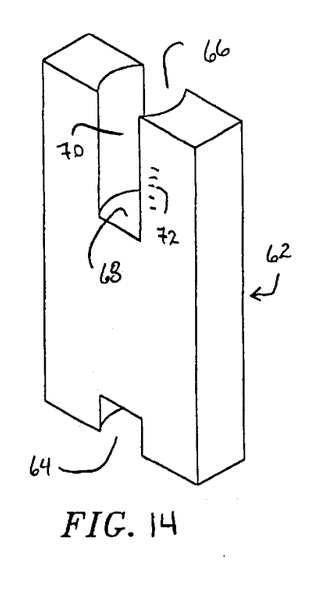
FIG. 14 is a perspective view of one embodiment of the presently disclosed outer diameter and length gauge.

Referring to FIG. 14, an in process check of the outside diameter and length of bone dowel 46 is performed to determine the adequacy thereof. Bone dowel 46 is placed in an appropriate outside diameter and length Go/No Go gauge 62. Bone dowel 46 is inserted into the No Go end 64 of gauge 62. If bone dowel 46 is acceptable (does not fit in No-Go end 64) proceed to check bone dowel 46 in the Go end 66 of gauge 62 by inserting bone dowel 46 into the Go end 66 of gauge 62 so that a slot of bone dowel 46 mates on a gauge boss 68 and medullary canal 18 is visible in window 70. If bone dowel 46 fits in the Go end 66 of gauge 62, the outside diameter is acceptable. If the outside diameter is acceptable, the length of bone dowel 46 can be checked by viewing length marker 72 to determine if the length falls within an acceptable range. If the length is acceptable, bone dowel 46 is acceptable. If bone dowel 46 fails, bone dowel 46 is rejected and dowel coring apparatus 10 should be checked. If the diameter of bone dowel 46 is acceptable, but the length is too long, bone dowel 46 is cut to a proper length and rechecked. If the length of bone dowel 46 is too short, bone dowel 46 is rejected.

The results of the above mentioned in-process checking procedures may be recorded on an attached log or the like.

Milling of Slot and Face

Figure 4:
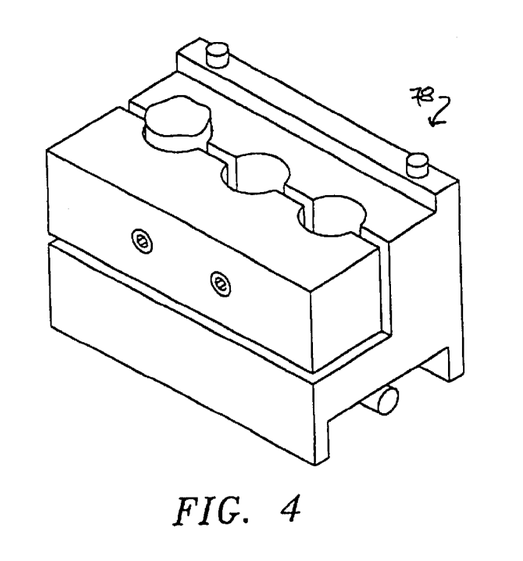
FIG. 4 is a perspective view of the holding block shown in FIG. 3 in the assembled condition.
Figure 5:
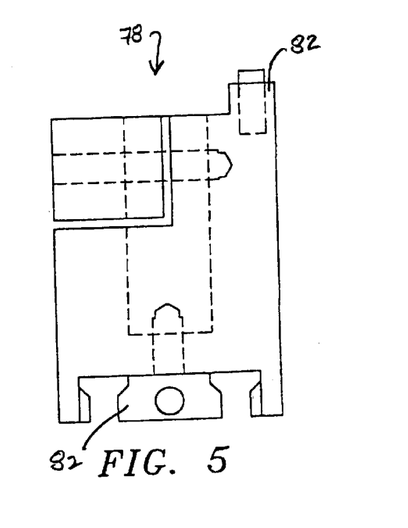
FIG. 5 is a side view of the holding block shown in FIG. 3.
Figure 6:
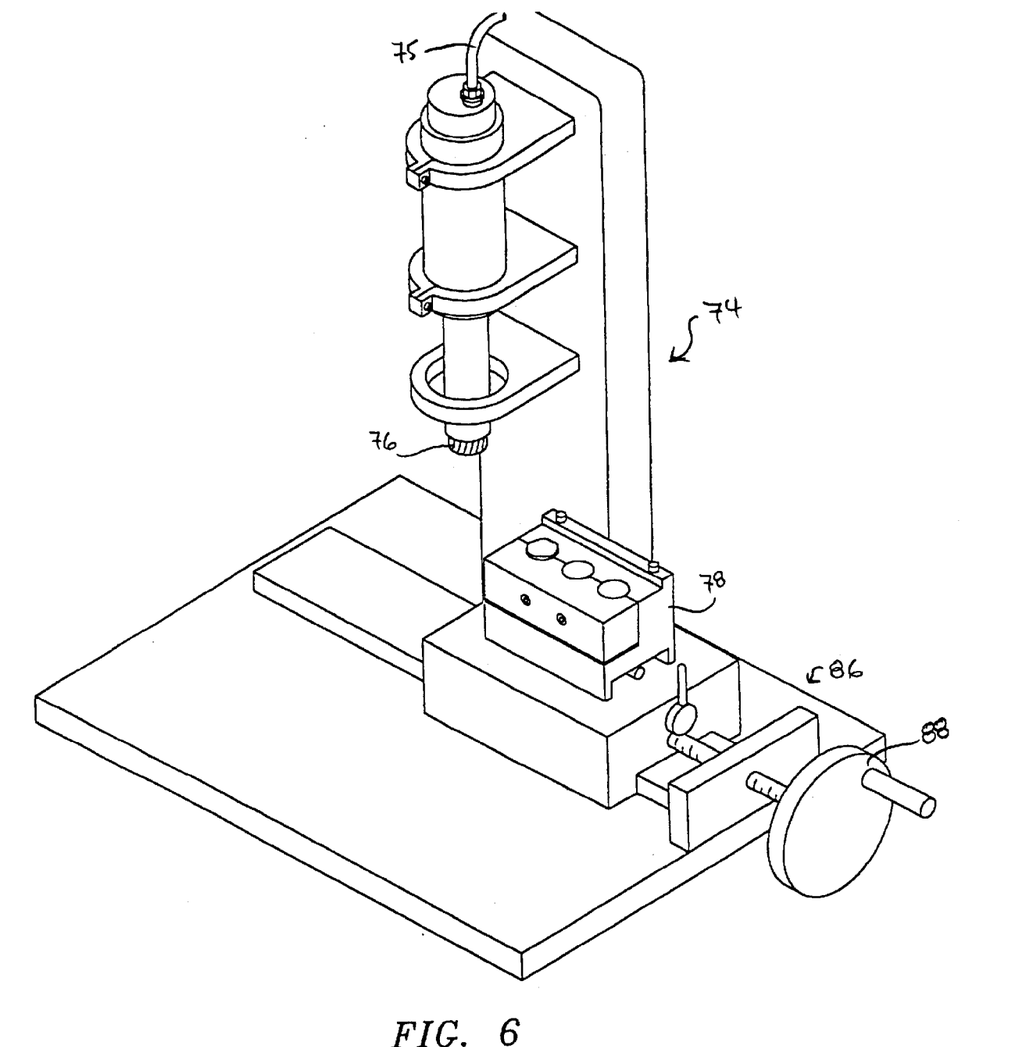
FIG. 6 is a perspective view of one preferred embodiment of the presently disclosed milling apparatus.

Referring to FIGS. 3–8, a dowel milling apparatus 74 is prepared and set up for operation during the manufacturing process by connecting an air supply 75 to dowel milling apparatus 74 (FIG. 6). Typically, a pressure of 100 psi and above is utilized, although milling apparatus requiring lower air pressures may also be used. A water supply (not shown) is connected to dowel milling apparatus 74 for irrigation.

Figure 8:
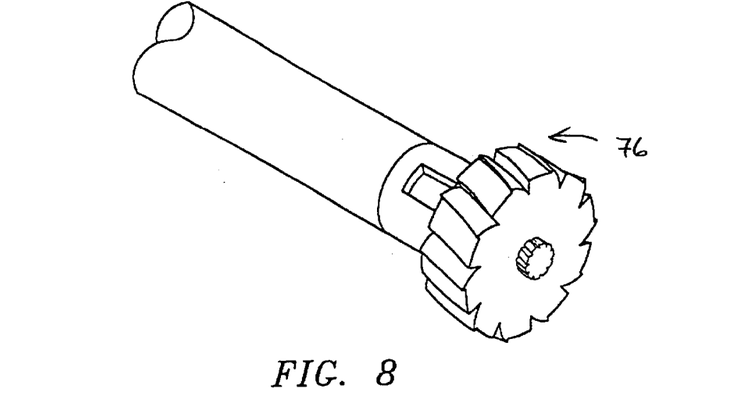
FIG. 8 is a perspective view of the slot milling bit of the milling apparatus shown in FIG. 6.

Referring to FIGS. 6 and 8, a face and slot milling bit 76 is secured to dowel milling apparatus 74. As a safety feature, air supply 75 should not be connected to apparatus 74 until the bit is secured to the dowel milling apparatus 74. Moreover, the water supply should only be turned on when using dowel milling apparatus 74.

Figure 3:
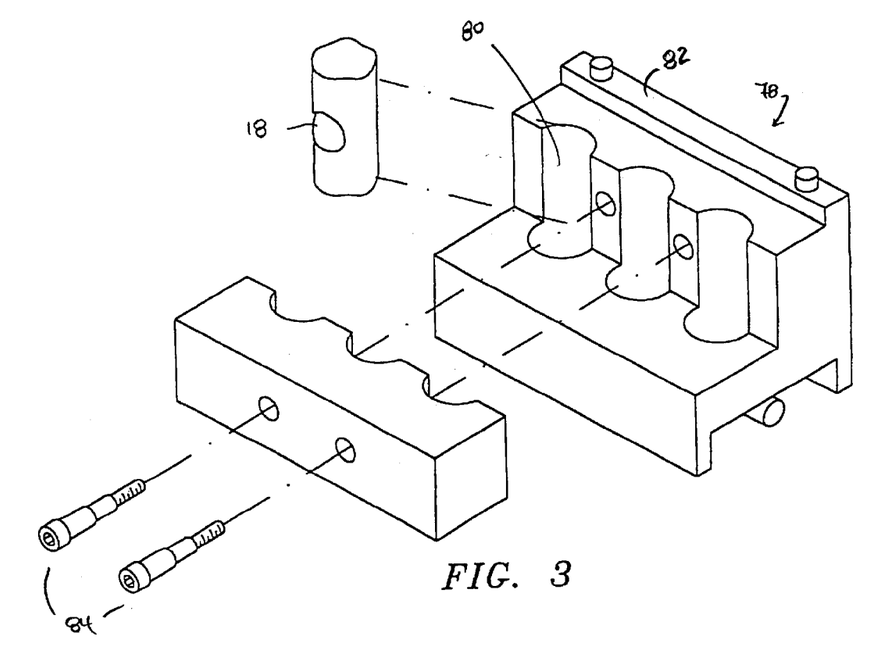
FIG. 3 is a perspective view with parts separated of a holding block of the presently disclosed dowel milling apparatus.

Referring to FIGS. 3–5, bone dowel 46 is inserted into an appropriately sized holding block 78. Bone dowel 46 is positioned in holding block 78 such that canal 18 is visible through block window 80 and the slot is milled approximately perpendicular to canal 18. The depth of bone dowel 46 as seated in block 78 is set with use of a guide 82 attached to block 78, as shown in FIG. 5. Set screws 84 are tightened so that block 78 holds bone dowel 46 securely in place. Up to three bone dowels can be placed into holding block 78 at one time. It is contemplated that holding block 78 may be alternately configured to hold a single or multiple number of bone dowels.

Referring back to FIG. 6, holding block 78 is inserted into a pre-centered vise 86 positioned on dowel milling apparatus 74 and vise 86 is secured.

Dowel milling apparatus 74 is activated by activating the water and air supplies. A handle 88 is manipulated to feed block 78 throughface and slot milling bit 76 in the forward and reverse directions. It is contemplated that bone dowel 46 should only pass through face and slot milling bit 76 forwards and reverse once. It is further contemplated that bone dowel 46 should not have reverse movement until face and slot milling bit 76 is completely clear of the last bone dowel in block 78. It is envisioned that prior to stopping dowel milling apparatus 74, face and slot milling bit 76 is clear of bone dowel 46. Dowel milling apparatus 74 is deactivated and holding block 78 is removed from vise 86.

Figure 7:
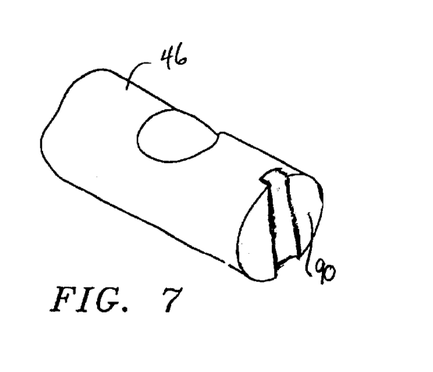
FIG. 7 is a perspective view of the bone dowel formed by the milling apparatus shown in FIG. 6.

Referring to FIG. 7, after the milling step described above, bone dowel 46 has a milled slot 90 and smooth face 91. Slot 90 is oriented substantially perpendicular to medullary canal 18. Bone dowel 46 may be removed from block 78.

Figure 13:
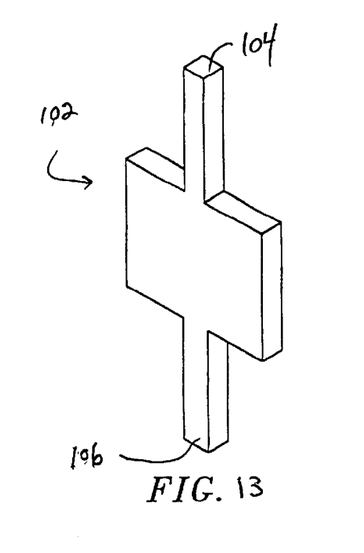
FIG. 13 is a perspective view of one embodiment of the presently disclosed slot width GO/NO GO gauge.

Referring to FIG. 13, an in process check of the slot width is performed using the universal Slot Width Go/No Go Gauge 102. Go side 104 of gauge 102 is inserted into slot 90 of bone dowel 46 so that it extends through the entire length of slot 90. If gauge 102 extends through the entire slot, it is acceptable. If it does not extend through the entire slot, bone dowel 46 is rejected. If bone dowel 46 is acceptable, proceed to check a No Go side 106 in the same manner. No Go side 106 should not fit into slot 90. Thus, if it does, slot 90 is too wide and bone dowel 46 is rejected. If No Go side 106 does not fit into slot 90, it is acceptable. If slot 90 is rejected, milling apparatus 74 should be checked. If bone dowel 46 is acceptable, proceed in the manufacturing process as follows.

Figure 16:
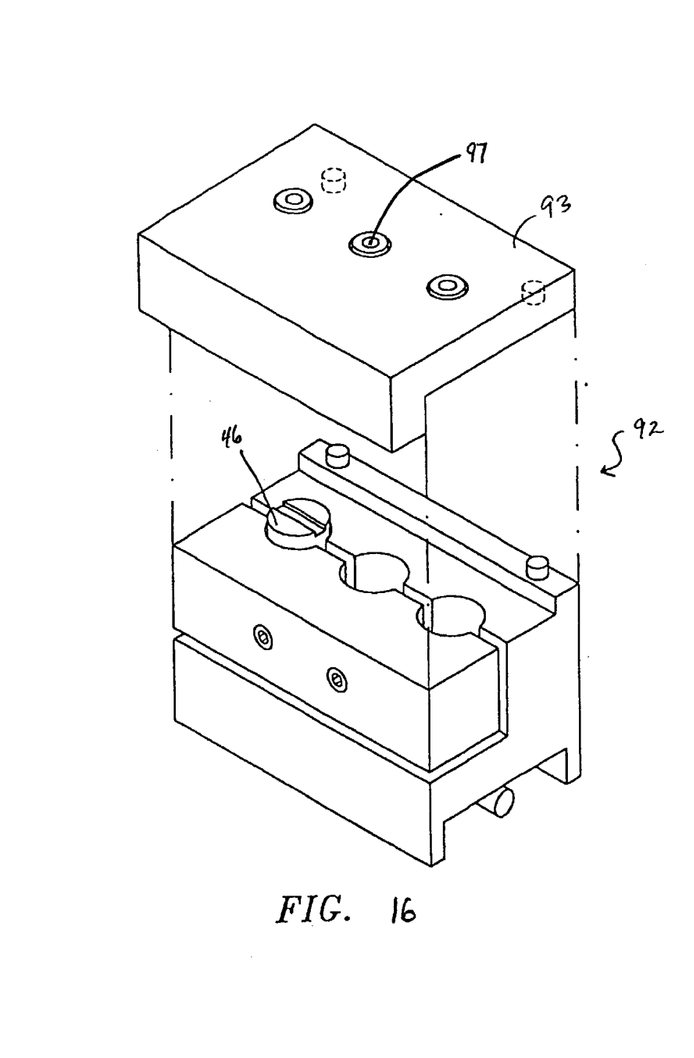
FIG. 16 is a perspective view with parts separated of one embodiment of the presently disclosed drilling holding block.
Figures 17, 18:
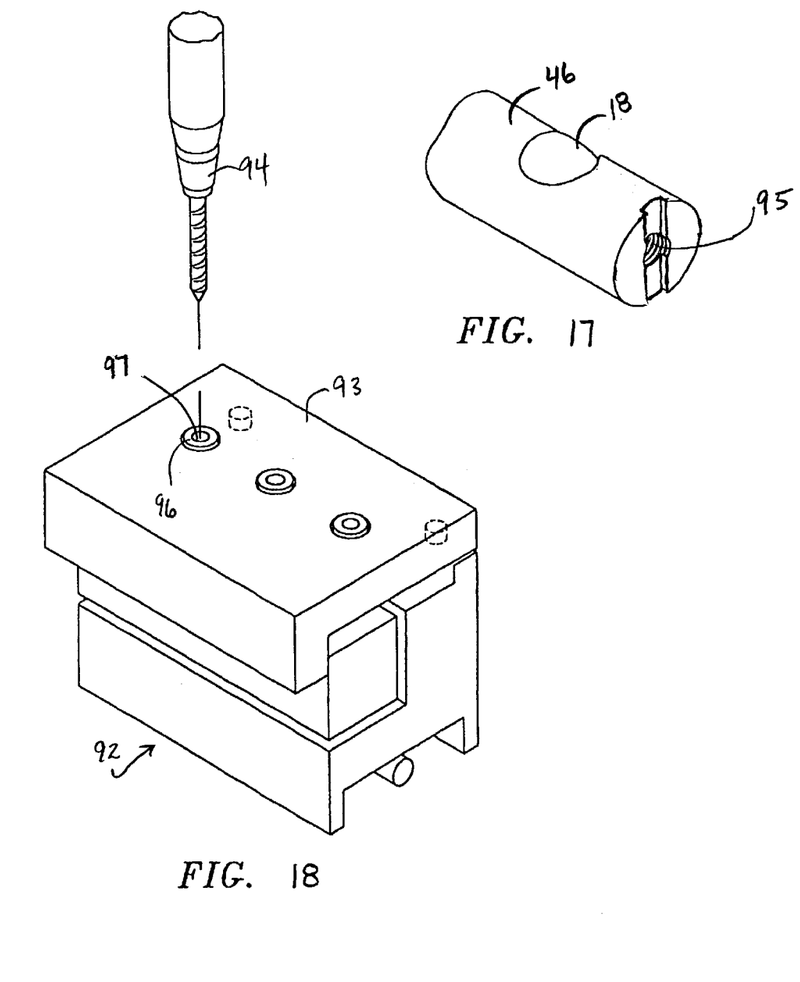
FIG. 17 is a perspective view of the bone dowel after the pilot hole has been drilled and tapped.
FIG. 18 is a perspective of the holding block shown in FIG. 16 in the assembled condition.

Referring to FIG. 16, bone dowel 46 is placed in a holding block 92 for drilling and tapping an insertion tool engaging bore 95. Bone dowel 46 is positioned with milled slot 90 on top. Up to three bone dowels can be placed into holding block 92 at one time. It is contemplated that holding block 92 may be alternately configured to hold a single or multiple number of bone dowels. Referring to FIG. 17, holding block 92 includes a drill centering device 93 having a guide bore 97 to facilitate proper positioning of a pilot hole drill bit 94 for drilling hole 95 in bone dowel 46.

Drill centering device 93 includes a drill guide 96 which defines guide bore 97 and cooperates with pilot hole drill bit 94 for drilling pilot hole 95. Pilot hole drill bit 94 is secured to an electric drill or the like. Manual activation of pilot hole drill bit 94 is also contemplated.

Pilot hole drill bit 94 is inserted through guide bore 97 to drill pilot hole 95. Drill bit 94 is rotated clockwise until drill bit 94 is observed through a holding block window (not shown) inside canal 18 of bone dowel 46 and drill bit 94 turns freely. Pilot hole drill bit 94 is removed by rotating drill bit 94 counter clockwise. Pilot hole drill bit 94 should not be advanced such as to engage the opposite wall of canal 18.

Figure 15:
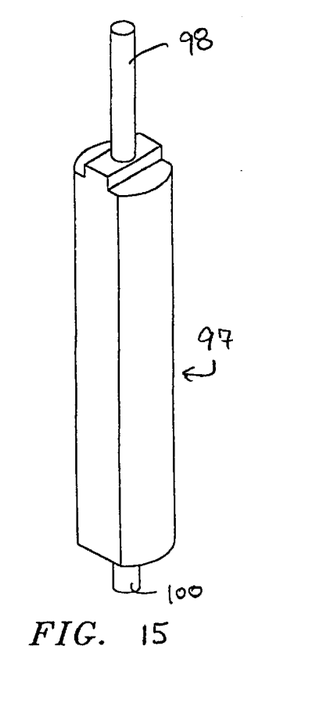
FIG. 15 is a perspective view of one embodiment of the presently disclosed pilot hole gauge.

Referring to FIG. 15, an in process check of pilot hole 95 of bone dowel 46 is performed to determine the adequacy of the inner diameter thereof. To accomplish this, pilot hole 95 is visually checked to ensure that it is approximately centered and that it passes into canal 18. Next, the inner diameter of pilot hole 95 is checked with Pilot Hole Pin Gauge 97. To accomplish this, end 98 of gauge 97 is inserted into pilot hole 95. Insertion should not be forced. If end 98 extends though pilot hole 95 and into canal 18, the diameter of pilot hole 95 is too large and bone dowel 46 is not acceptable. If pilot hole 95 does not extend into canal 18, it can be drilled through using a hand held tool and rechecked for proper inner diameter, as discussed above.

Figures 19, 20, 21, 22:
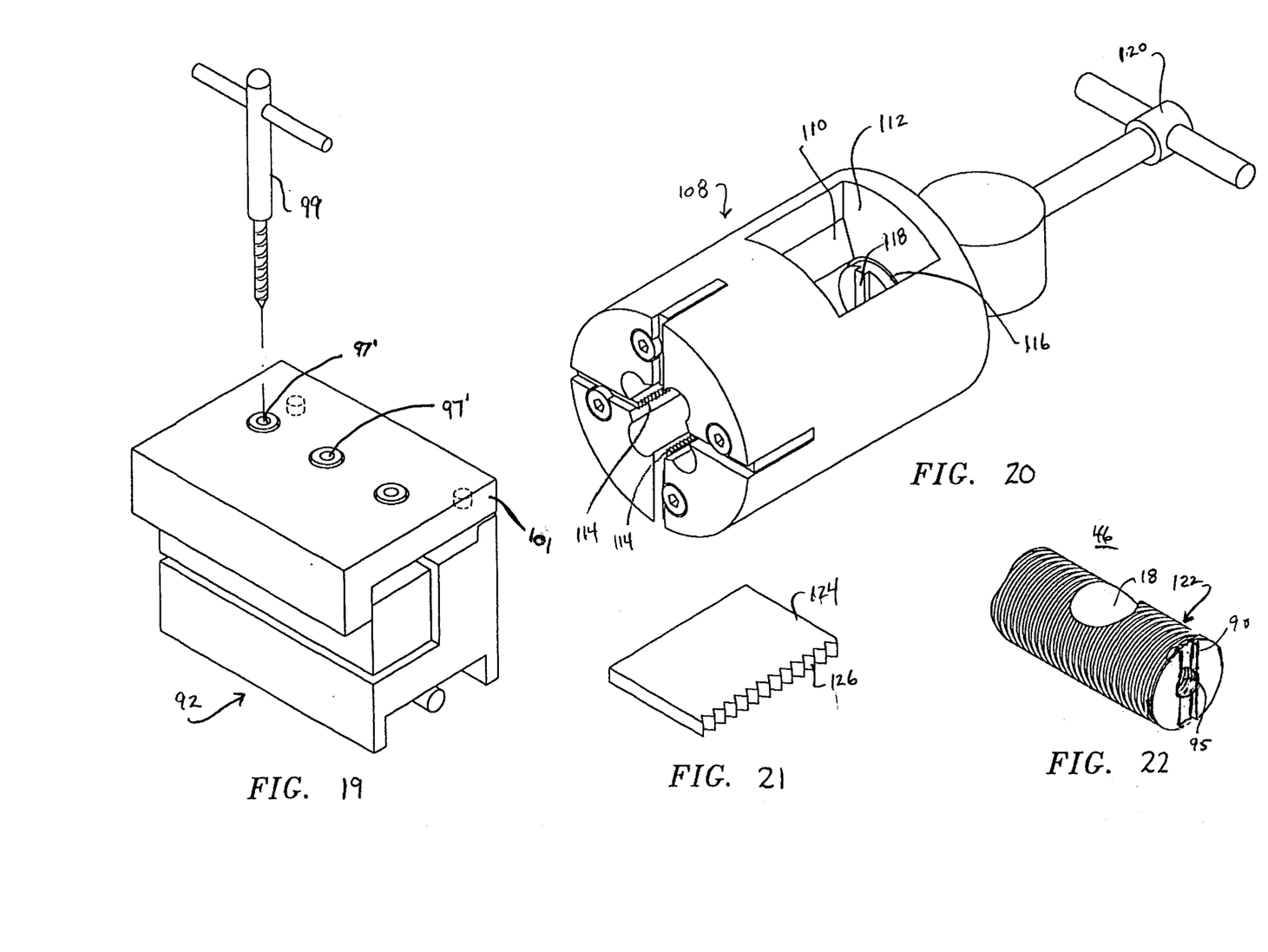
FIG. 19 is a perspective view of one embodiment of the presently disclosed tapping holding block.
FIG. 20 is a perspective view of the presently disclosed dowel threading tool.
FIG. 21 is a perspective view of a presently disclosed dowel thread gauge.
FIG. 22 is a perspective view of a threaded bone dowel after the outer surface has been threaded using the dowel threading tool shown in FIG. 20.

Referring to FIG. 19, pilot hole 95 is now threaded. To accomplish this, a tap centering device 101 is secured to mounting block 92. Tap centering device 101 is similar to drill centering device 93 except that guide bore 97' is larger than guide bore 97 to allow passage of tap 99. A tap 99 is inserted through guide bore 97' of device 101 to thread pilot hole 95 of bone dowel 46. Tap 99 is removed after this is accomplished by manually twisting tap 99 counter clockwise from guide bore 97'. It is contemplated that tap 99 may be operated by motorized means. It is further contemplated that tap 99 should not be inserted so far as to engage the opposite wall of canal 18.

Bone dowel 46 can now be removed from holding block 92. Bone dowel 46 is rinsed in water to remove loose bone particles from its exterior and medullary canal 18. Referring to FIG. 18, bone dowel 46 now includes internally threaded pilot hole 95. Referring again to FIG. 15, an end 100 of gauge 97 may be used to check the adequacy of the threads of pilot hole 95.

An in-process check of the cortical face wall thickness of bone dowel 46 may be conducted using the universal wall thickness Go/No Go gauge 48, similar to that described above with regard to FIGS. 12a–12c. If the face wall thickness of bone dowel 46 is unacceptable, reject bone dowel 46 and recheck slot and face milling bit 76 and placement in holding block 78. Also reassess the suitability of the donor bone being used for dowel production. If acceptable, proceed in the manufacturing process.

Threading

Referring to FIGS. 20 and 21, bone dowel 46 can now be externally threaded. A threading tool 108 is prepared and set up for operation during the manufacturing process. A water supply (not shown) is connected to threading tool 108 for irrigation. It is contemplated that the water supply should be activated only when threading tool 108 is in use. It is further contemplated that threading tool 108 may be configured for a variety of different size bone dowels, such as, for example, 14 mm, 16 mm, 18 mm, 20 mm, etc. Bone dowel 46 is positioned onto a loading shelf 110 within threading tool 108 through a window 112 formed in tool 108. Threading tool 108 includes a plurality of circumferentially spaced inserts 114 having teeth for engaging and threading the exterior cylindrical surface of bone dowel 46. A driver 116 engages the slotted end of bone dowel 46 to drive bone dowel 46 through threading tool 108 to form the threads on the exterior of bone dowel 46. Bone dowel 46 is placed onto driver 116 such that a tang 118 located at an end of driver 116 engages slot 90 of bone dowel 46.

Tang 118 is configured to engage slot 90 of bone dowel 46 to manually advance bone dowel 46 through tool 108 by turning a handle 120 clockwise. When bone dowel 46 has passed entirely through threading tool 108, it will discharge from tool 108 into a cradle or the like (not shown) positioned at one end of tool 108. Bone dowel 46 should not be backed through threads 114 of tool 108 once it has passed through initially, nor should bone dowel 46 be run through twice. Referring to FIG. 21, bone dowel 46 now includes external threads 122.

Referring to FIG. 22, an in process check of threads 122 of bone dowel 46 is performed to determine the adequacy thereof. To accomplish this, dowel threads 122 are checked using thread check gauge 124 which includes verifying threads 126. Verifying threads 126 are aligned with dowel threads 122 and threads 122 of bone dowel 46 are visually checked for gaps, unevenness, and improper fit. If gauge 124 fits threads 122 without gaps and unevenness, threads 122 are acceptable. If threads 122 are unacceptable, bone dowel 46 is rejected and threading tool 108 is inspected for quality and adjusted. If threads 122 are acceptable, proceed in the manufacturing process as follows:

An in-process check of the outside diameter and length of bone dowel 46 may be conducted using outside diameter and length gauge 62, similar to that described above with regard to FIG. 14. After completion of the above method, each acceptable bone dowel 46 is sterility tested, measured and packaged for use.

It will be understood that various modifications may be made to the embodiments disclosed herein. For example, the double sided gauges shown in FIGS. 14–17 can be formed as two separate gauges. The gauges may also be provided in a kit for forming bone dowels having any desired dimensions. Moreover, the coring and milling apparatus can be electrically, hydraulically, or pneumatically actuated apparatus. Therefore, the above description should not be construed as limiting but exemplifications of the various embodiments. One skilled in the art will envision other modifications within the scope and spirit of the claims appended hereto.

What is claimed is:

1. A method for manufacturing a bone dowel from a bone shaft defining a medullary canal, the method comprising the following steps:

a) coring a cylindrical dowel from the bone shaft such that the medullary canal of the bone shaft forms a throughbore in the dowel having an axis which is transverse to the longitudinal axis of the dowel;

b) performing an in-process inspection of wall thickness of the dowel;

c) rejecting the dowel if the dowel wall thickness does not have at least predetermined dimensions suitable for implant use; and d) forwarding the dowel for further machining if the dowel has dimensions greater than the predetermined dimensions suitable for implant use.

2. A method according to claim 1, wherein the step of performing an in-process inspection of the wall thickness of the dowel includes inspecting the sidewall thickness of the dowel.

3. A method according to claim 1 wherein the step of performing an in-process inspection of the wall thickness of the dowel includes inspecting the thickness of the top and bottom walls of the dowel.

* * * * *